United States Patent [19]
Byrne et al.

[11] Patent Number: 5,925,572
[45] Date of Patent: Jul. 20, 1999

[54] APPARATUS AND METHOD FOR IN SITU PH MEASUREMENT OF AQUEOUS MEDIUM

[75] Inventors: Robert H. Byrne, St. Petersburg; Robert D. Waterbury, Palm Harbor; John J. Kelly; Bram Leader, both of Clearwater; Randy Russell, Safety Harbor; Charles W. Jones, Seminole; Joseph R. Kolesar, Pinellas Park, all of Fla.; Sean McElligott, Bryn Mawr, Pa.

[73] Assignee: University of South Florida, Tampa, Fla.

[21] Appl. No.: 08/907,324

[22] Filed: Aug. 6, 1997

Related U.S. Application Data

[60] Provisional application No. 60/023,553, Aug. 7, 1996.

[51] Int. Cl.$^6$ .......................... G01N 21/80; G01N 21/00
[52] U.S. Cl. ..................... 436/163; 324/438; 356/319; 364/528.02; 422/55; 422/82.09; 436/164
[58] Field of Search .......................... 210/94, 96.1, 742, 210/743, 745; 356/319, 326; 364/528.01, 528.02; 422/82.05, 82.09, 55; 436/39, 161, 163, 164, 171; 324/438

[56] References Cited

U.S. PATENT DOCUMENTS 5,242,602  9/1993  Richardson et al. ..................... 210/745
5,528,363  6/1996  Fachinger et al. ...................... 356/326

FOREIGN PATENT DOCUMENTS

WO 93/04366  3/1993  WIPO ..................................... 436/39
WO 95/01560  1/1995  WIPO ................................. 422/82.09

*Primary Examiner*—Joseph W. Drodge
*Attorney, Agent, or Firm*—Allen, Dyer, Doppelt, Milbrath & Gilchrist, P.A.

[57] ABSTRACT

A pH sensor based upon spectrophotometric techniques has been developed for in situ analysis of an aqueous medium, e.g., surface seawater. This sensor utilizes a spectrophotometric pH indicator (Thymol Blue), which has been calibrated for use in seawater as a function of temperature and salinity. Shipboard spectrophotometric pH analyses routinely demonstrate a precision on the order of ±0.0004 pH units. In situ analysis of seawater pH has demonstrated a precision on the order of ±0.001 and an accuracy, using shipboard measurements as a standard, on the order of ±0.01. The sensor is a self-contained system that pumps seawater, meters in indicator, and spectrophotometrically determines indicator absorbance cells, each with three wavelength channels, to obtain the spectrophotometric absorbance. The sensor system, rated for depths up to 500 m, provides pH, conductivity, and temperature and can be operated via computer or in a standalone mode with internal data storage. The sensor utilizes less than 12 watts of power and is packaged in an aluminum housing.

7 Claims, 11 Drawing Sheets

APPARATUS AND METHOD FOR IN SITU PH MEASUREMENT OF AQUEOUS MEDIUM

CROSS-REFERENCE TO RELATED APPLICATION

This application claims priority from provisional application Ser. No. 60/023,553, "Apparatus and Method for in situ pH Measurement of Aqueous Medium," filed Aug. 7, 1996.

GOVERNMENT SUPPORT

This work was supported by the Office of Naval Research through Grant No. N00014-94-0963 and by the National Oceanic and Atmospheric Administration through Grant No. NA56GP0305.

SUMMARY OF THE INVENTION

The present invention, in one of its broadest aspects, relates to an apparatus and method for in situ pH measurement of an aqueous medium. The invention provides for determining the salinity and temperature of the aqueous medium, adding an indicator to the aqueous medium, and utilizing spectrophotometric analysis of the absorption characteristics of the aqueous medium/indicator mixture to determine the pH of the aqueous medium.

Moreover, the present invention provides an apparatus and method for in situ pH measurement of an aqueous medium, in which a substantially continuous flow of the aqueous medium can be analyzed with a frequency that effectively provides for near-real-time pH analysis of the aqueous medium.

According to the preferred form of the present invention, a pH sensor comprises a specially designed vessel which is designed to be immersed in an aqueous medium, e.g. a body of seawater. The vessel has a sealed portion and a wet portion. The sealed portion contains electronic and opto-electronic components. The wet portion comprises (i) one or more probes in direct contact with the aqueous medium, and (ii) an optical flow channel through which a portion of the aqueous medium in which the vessel is immersed is directed at a substantially continuous, controlled rate. An indicator (e.g., a dye) is introduced into the aqueous medium at a predetermined location in the optical flow channel, to form an aqueous medium/indicator mixture in the optical flow channel. The opto-electronic components are oriented to the optical flow channel to provide optical power inputs related to the absorbance characteristics of the aqueous medium/indicator mixture in the optical flow channel. The electronic components are adapted to receive and process inputs from the probes and opto-electronic components at a frequency rate (e.g., at about one-second intervals) which enables substantially continuous determination of the pH of the aqueous medium in which the vessel is immersed.

Preferably, the temperature, salinity and optical power inputs are sampled and processed at the foregoing frequency rate, and processed data is then transmitted (via data transmission lines) from the vessel to a receiving station remote from the vessel. For example, the receiving station could be a computer located onboard a ship from which the vessel is deployed, and which computer receives the processed data, performs the final pH calculations, and produces output (e.g., data and/or graphical) related directly to the pH of the aqueous medium.

Also, according to the preferred embodiment, the indicator (e.g., thymol blue) is one that, when introduced into the aqueous medium, comes quickly to chemical equilibrium with the aqueous medium, to enable the optical power inputs to be made and processed with the desired frequency.

Further features of the present invention will become apparent from the following detailed description and the accompanying drawings.

The following example describes a preferred embodiment of the present invention, in an in situ system for pH measurement of sea water. The temperature, salinity, and optical absorbance data were provided at about 1 second intervals, and total throughput time intervals of about 6 seconds, thereby demonstrating the capabilities of the embodiment for near-real-time performance.

I. BACKGROUND OF THE INVENTION/PRIOR ART

1.1 Objectives

The goal of this project was development of an in situ sensor with capabilities for examining oceanic pH microstructure. Spectrophotometric procedures have been developed for analysis of seawater pH because of the extraordinary precision, convenience, and reproducibility of such measurements. Shipboard spectrophotometric pH measurements routinely exhibit a precision of ±0.0004 pH units. Alternative procedures for measurement of seawater pH are being developed that will ultimately result in small robust sensors with relatively low sampling frequency (i.e., immobilized dyes on polymer films, etc.). However, to study oceanic microstructure, precise and rapid in situ measurements of seawater pH are required.

These prior art procedures are described in the following literature:

G. L. Robert-Baldo, M. J. Morris, and R. H. Byrne, "Spectrophotometric Determination of Seawater pH Using Phenol Red", Analytical Chemistry 57, pp. 2564–67, 1985;

R. H. Byrne, "Standardization of Standard Buffers by Visible Spectrometry", Analytical Chemistry 59, pp. 1479–81, 1987;

R. H. Byrne and R. H. Breland, "High Precision Muti-wavelength pH Determinations in Seawater Using Cresol Red", Deep-Sea Research 36(5), pp. 803–10, 1989;

T. D. Clayton and R. H. Byrne, "Spectrophotometric pH Measurements: Total Hydrogen Ion Concentration Scale Measurements and At-Sea Results", Deep-Sea Research 40, pp. 2315–29, 1993;

H. Zhang and R. H. Byrne, "Spectrophotometric pH Measurements of Surface Seawater In-Situ Conditions: Absorbance and Protonation Behavior of Thymol Blue", Marine Chemistry 52, pp. 17025, 1996;

J. R. V. Zaneveld, J. C. Kitchen, A. Bricaud, and C. Moore, "Analysis of In-Situ Spectral Adsorption Meter Data", Ocean Optics XI, Gary D. Gilbert, Editor, Proc. SPIE 1750, pp.187–99, 1992; and J. R. V. Zaneveld, J. C. Kitchen, and C. Moore, "The Scattering Error Correction of Reflecting-Tube Absorption Meters", Ocean Optics XII, Jules S. Jaffe, Editor, Proc. SPIE 2258, pp. 44–55, 1994.

DETAILED DESCRIPTION OF THE INVENTION

According to the preferred form of the present invention, the sensor comprises a specially designed vessel $10$ which is immersed in an aqueous medium, e.g., a body of seawater. The vessel $10$ has a sealed portion $12$ and a wet portion $14$. The sealed portion $12$ comprises a pair of sealed compartments $12A$, $12B$ coupled together by struts $12C$. The sealed section $12$ contains electronic components (e.g., main control board $16$, microcontroller $18$, Lon board $20$, CTD electronic component $22$, pump circuit control board $24$, motor $26$) and opto-electronic components (e.g., light-emitting diodes or LED's $28$ and associated detectors $30$). The wet portion comprises (i) probes $32$, $34$ in direct contact with the aqueous medium, and (ii) an optical flow channel $36$ disposed between the sealed compartments $12A$, $12B$, and through which a portion of the aqueous medium in which the vessel is immersed is directed at a substantially continuous, controlled rate. The aqueous medium is directed through the optical flow channel by means of a gear pump $38$ which draws the aqueous medium into and through a "no dye" optical cell $40$ in the upstream portion of the optical flow channel, mixes the aqueous medium with an indicator (preferably a thymol blue dye), and pushes the aqueous medium/indicator mixture through a "dye" optical cell $42$ in the downstream portion of the optical flow channel. The dye is directed to the gear pump $38$ by means of a dye pump $44$.

Figure 1:
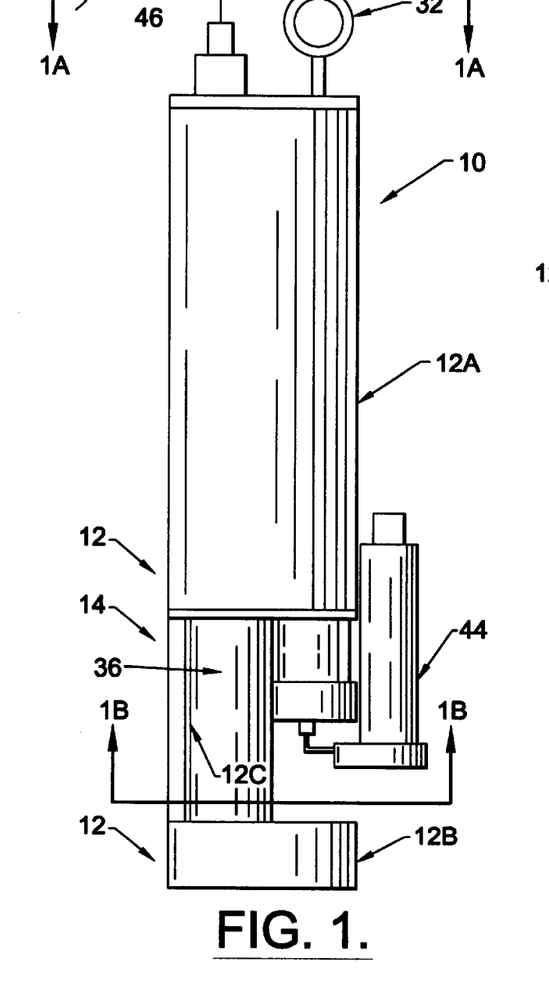
FIG. 1 is a schematic side view of a vessel for immersion in an aqueous medium, e.g., seawater, for use in providing substantially continuous determination of the pH of the aqueous medium, in accordance with the present invention.
Figure 2:
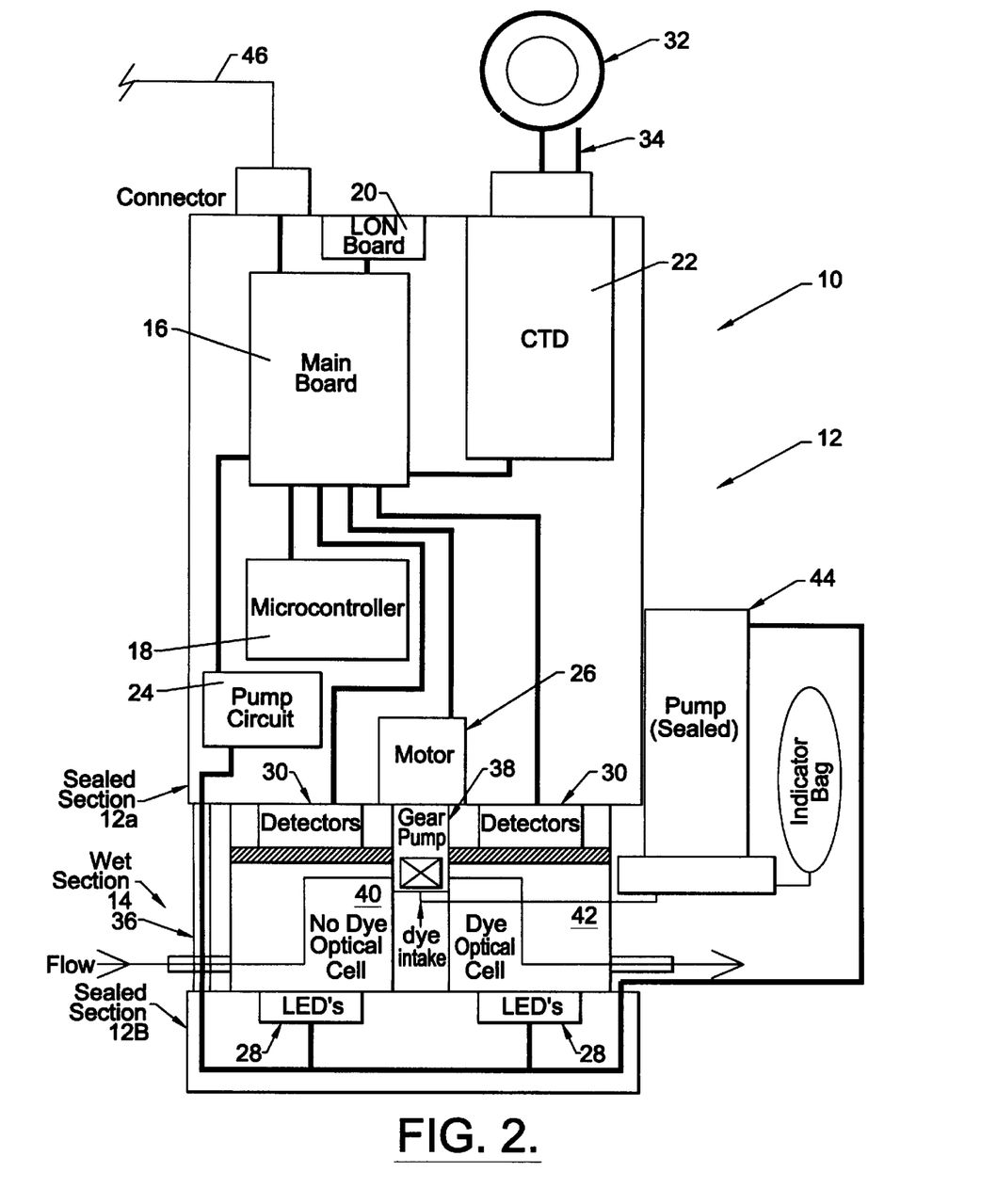
FIG. 2 is a schematic block diagram of the major components of the vessel of FIG. 1.
Figure 3:
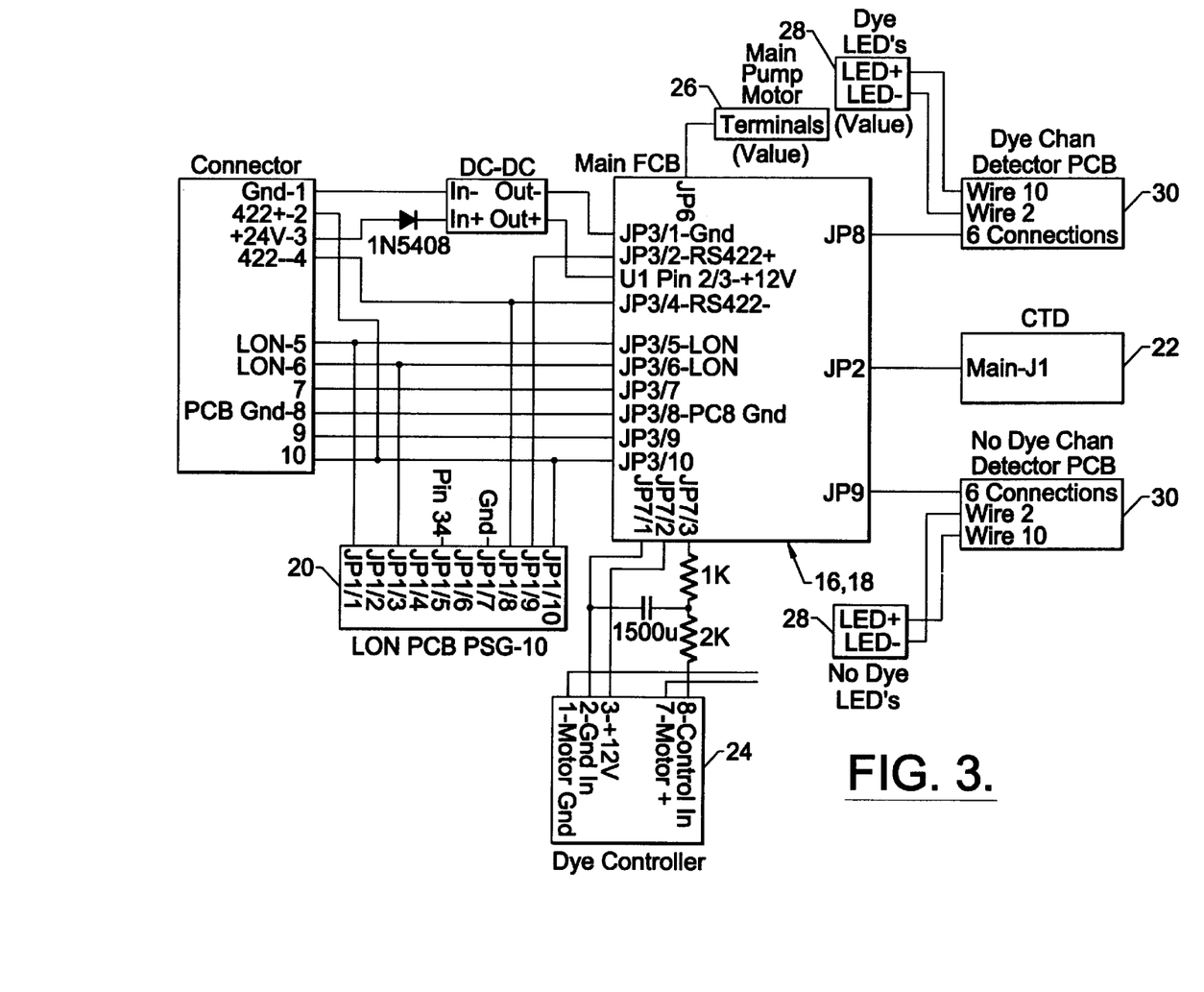
FIG. 3 is a block wiring diagram of the circuitry for the electron and opto-electron components of the vessel of FIGS. 1 and 2.
Figure 4:
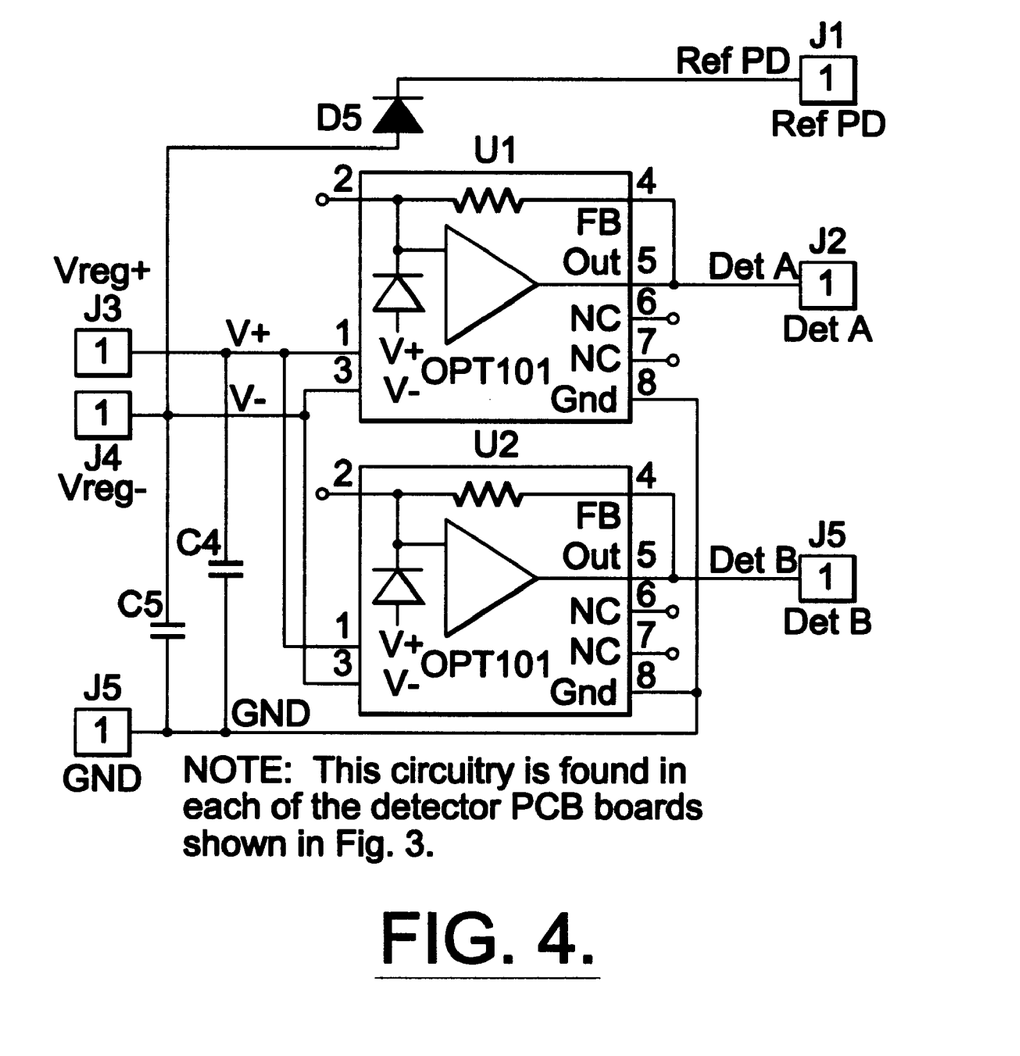
FIG. 4 is a circuit diagram of the detector circuit boards for the vessel of FIGS. 1 and 2.
Figure 5A:
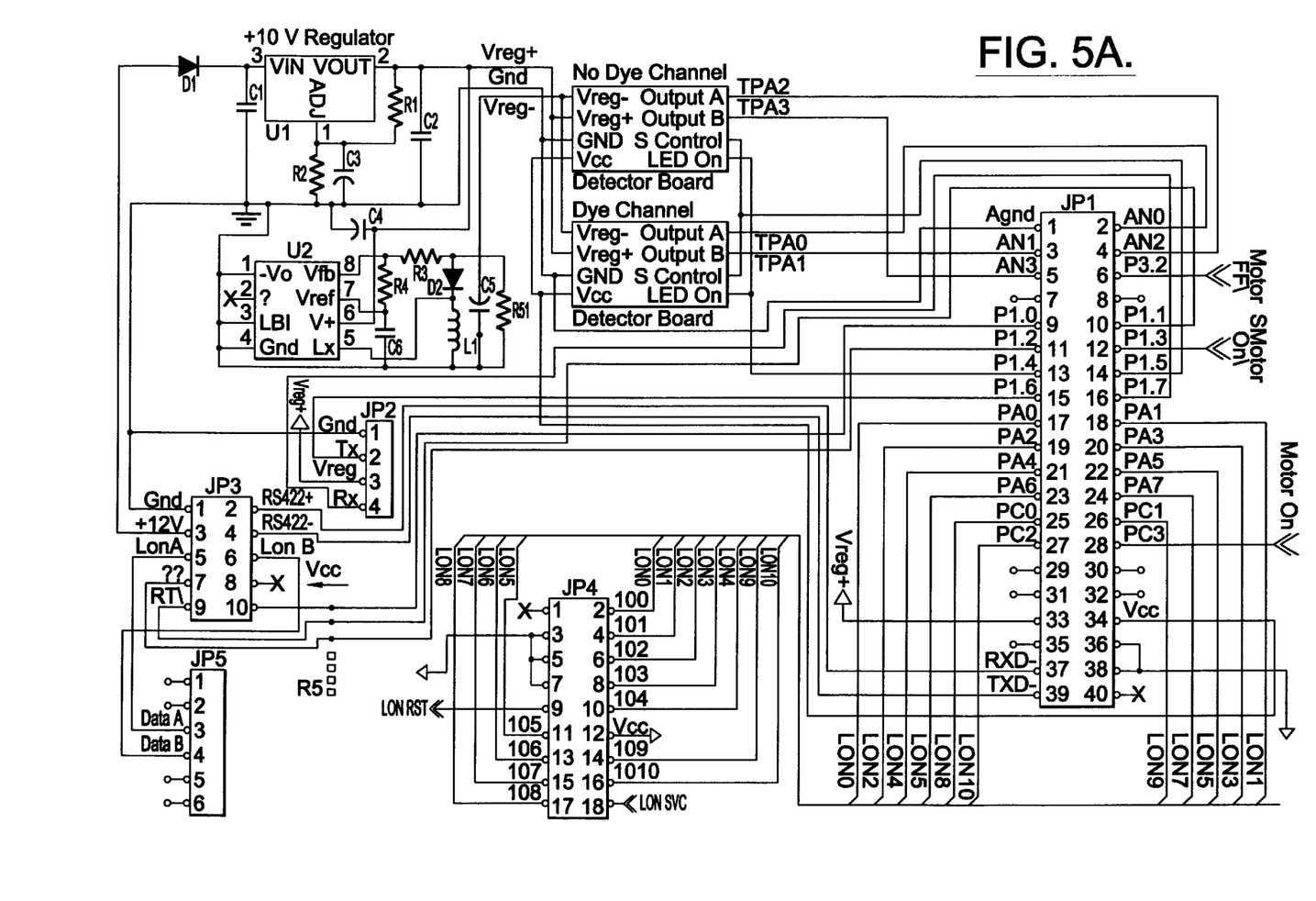
FIGS. 5A–D are circuit diagrams of the main control board and microcontroller for the vessel of FIGS. 1 and 2.
Figure 5B:
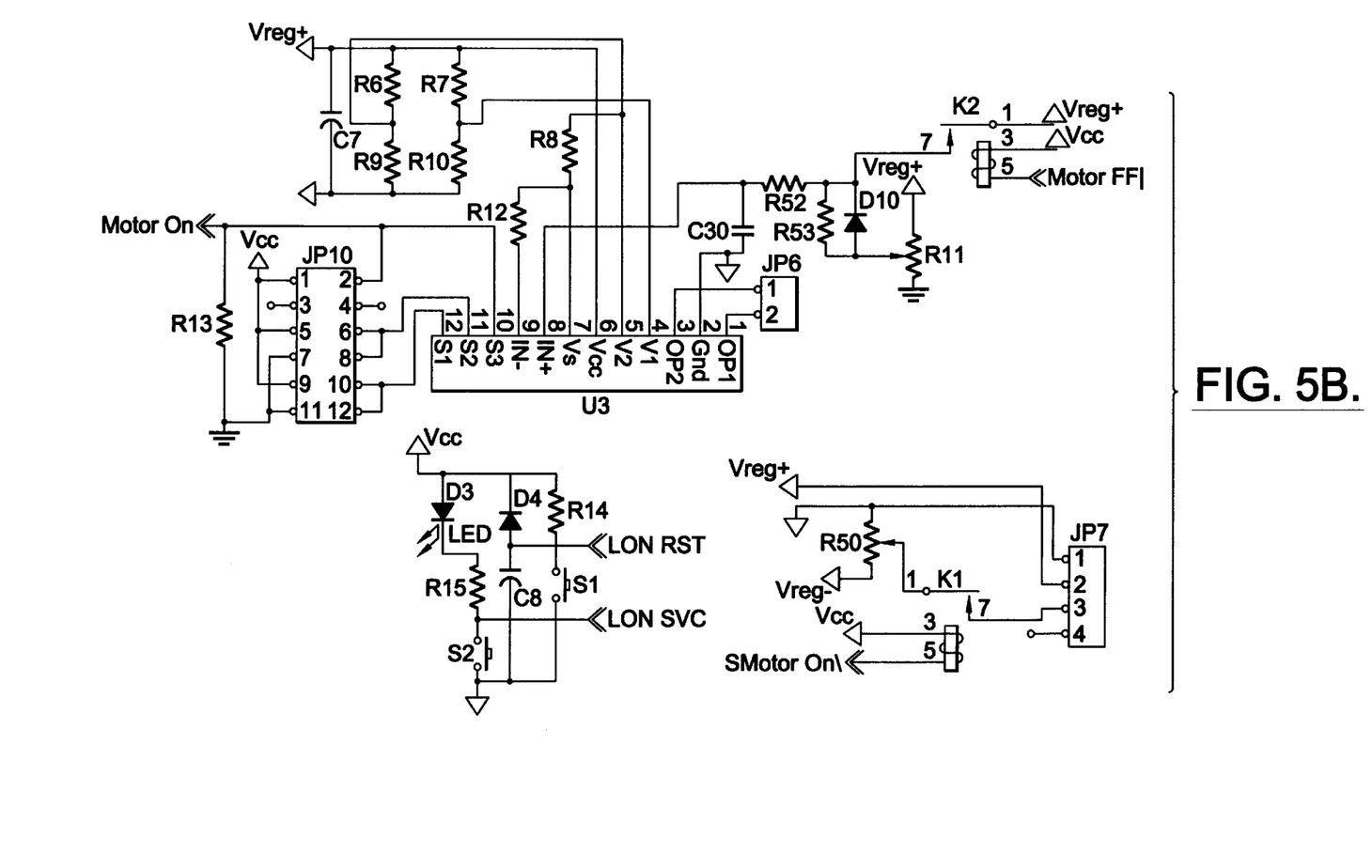
Figure 5C:
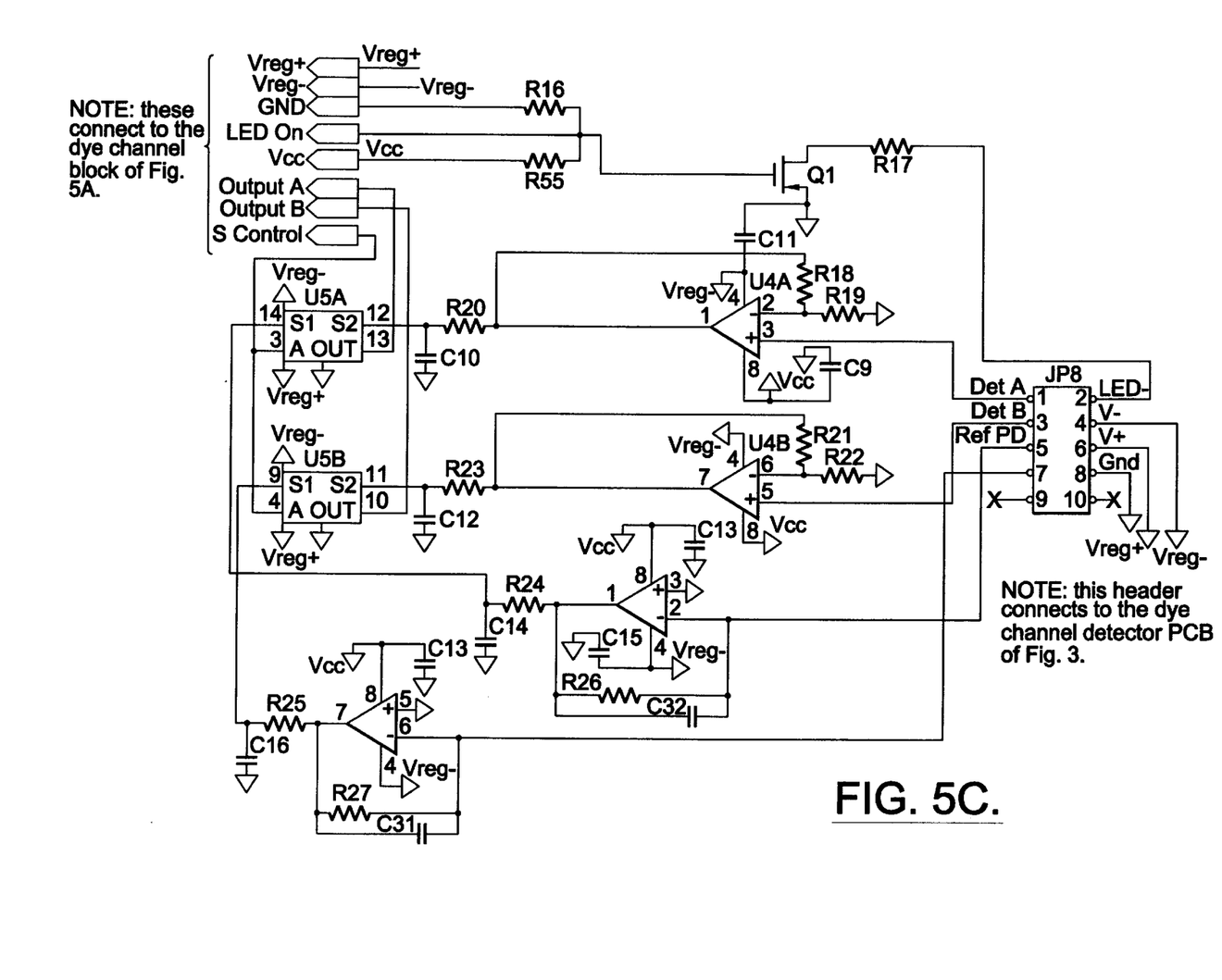
Figure 5D:
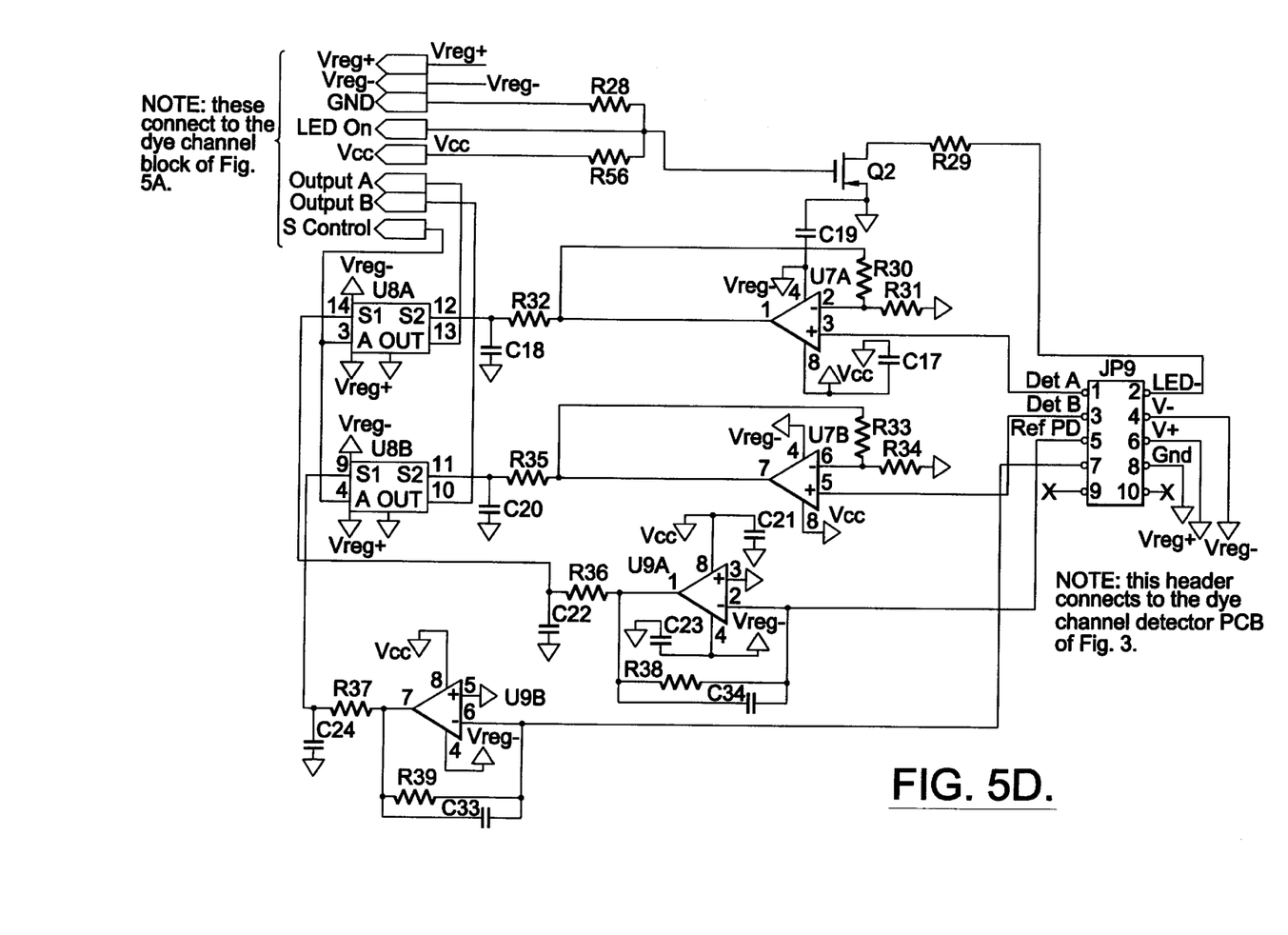
Figure 6:
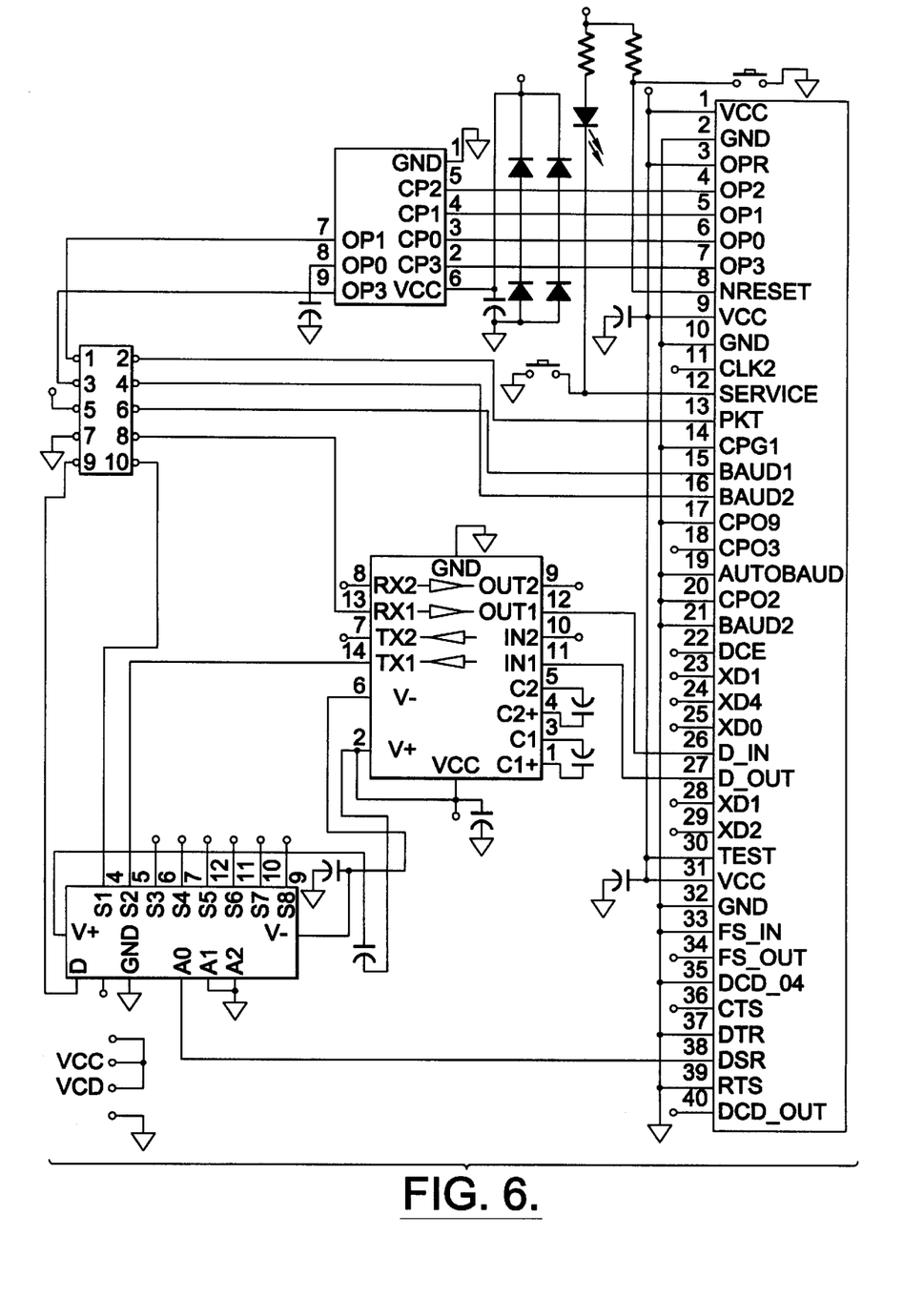
FIG. 6 is a circuit diagram of the Lon circuitry for the vessel of FIGS. 1 and 2.

The opto-electronic components (i.e., LED's $28$ and detectors $30$) are associated with each of the "no dye" and "dye" optical cells $40$, $42$. The opto-electronic components provide optical power inputs to the main control board $16$ related to the absorbance characteristics of the aqueous medium and aqueous medium/indicator mixture. The probes $32$, $34$ provide inputs related to the temperature and salinity of the aqueous medium to the electronic components (i.e., to the CTD $22$). The inputs from the probes and the opto-electronic components are sampled and processed at a frequency (i.e., at about one-second intervals), to provide the data which is then used in the final pH calculations. The sampling of inputs at such a frequency is believed to enable what would be recognized by those in the art as substantially continuous determination of the pH of the aqueous medium.

The data sampled and collected in the sealed portion $12$ of the vessel can be transmitted (via data transmissions lines $46$) to a receiving station (not shown) remote from the aqueous medium. For example, the receiving station could be a personal computer (PC) onboard a ship from which the vessel $10$ is deployed. The computer receives the data, performs the final pH calculations, and produces output (e.g., data and/or graphical) related to the pH of the aqueous medium, as illustrated with reference to FIG. 7.

Also, according to the preferred embodiment, the indicator (e.g., thymol blue) is one that, when introduced into the aqueous medium, comes quickly to chemical equilibrium with the aqueous medium, to enable the optical power inputs to be made and processed with the desired frequency.

1.2 Measurement Technique

Thymol blue was selected as an ideal indicator for this sensor based upon the compatibility of its indicating range with the relatively high pH of the surface ocean and because it comes quickly to chemical equilibrium with seawater. Seawater pH is determined through absorbance, salinity, and temperature observations using the following equations:

$$pH_T = pK_2 + \log[(R-e_1)/(e_2-Re_3)]$$

$$pK_2 = 4.706 \cdot S/T + 26.3300 - 7.17218 \cdot \log(T) - 0.017316 \cdot S$$

$$e_1 = -0.00132 + 1.600 \times 10^{-5} \cdot T$$

$$e_2 = 7.2326 - 0.0299717 \cdot T + 4.600 \times 10^{-5} \cdot T^2$$

$$e_3 = 0.0223 + 3.917 \times 10^{-4} \cdot T$$

$$R = {}^{596}A/{}^{435}A$$

where ${}^{\lambda}A$ is the optical absorbance of Thymol blue at wavelength $\lambda$ (nm), S is salinity, and T is temperature in K.

2.1 Instrument Development and Design

Figure 1A:
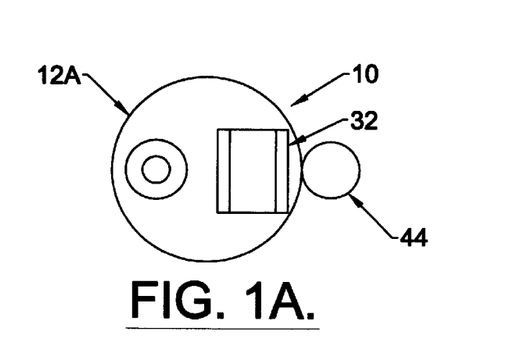
FIG. 1A is a top view of a portion of the vessel of FIG. 1, taken from the direction 1A—1A.
Figure 1B:
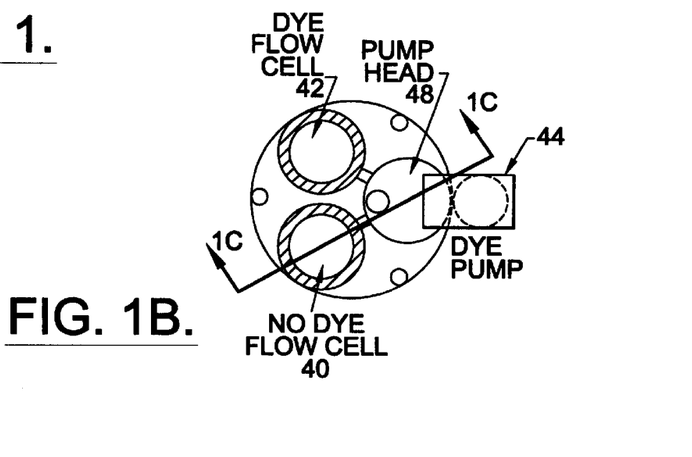
FIG. 1B is a sectional view of the vessel of FIG. 1, taken from the direction 1B—1B, with portions omitted.
Figure 1C:
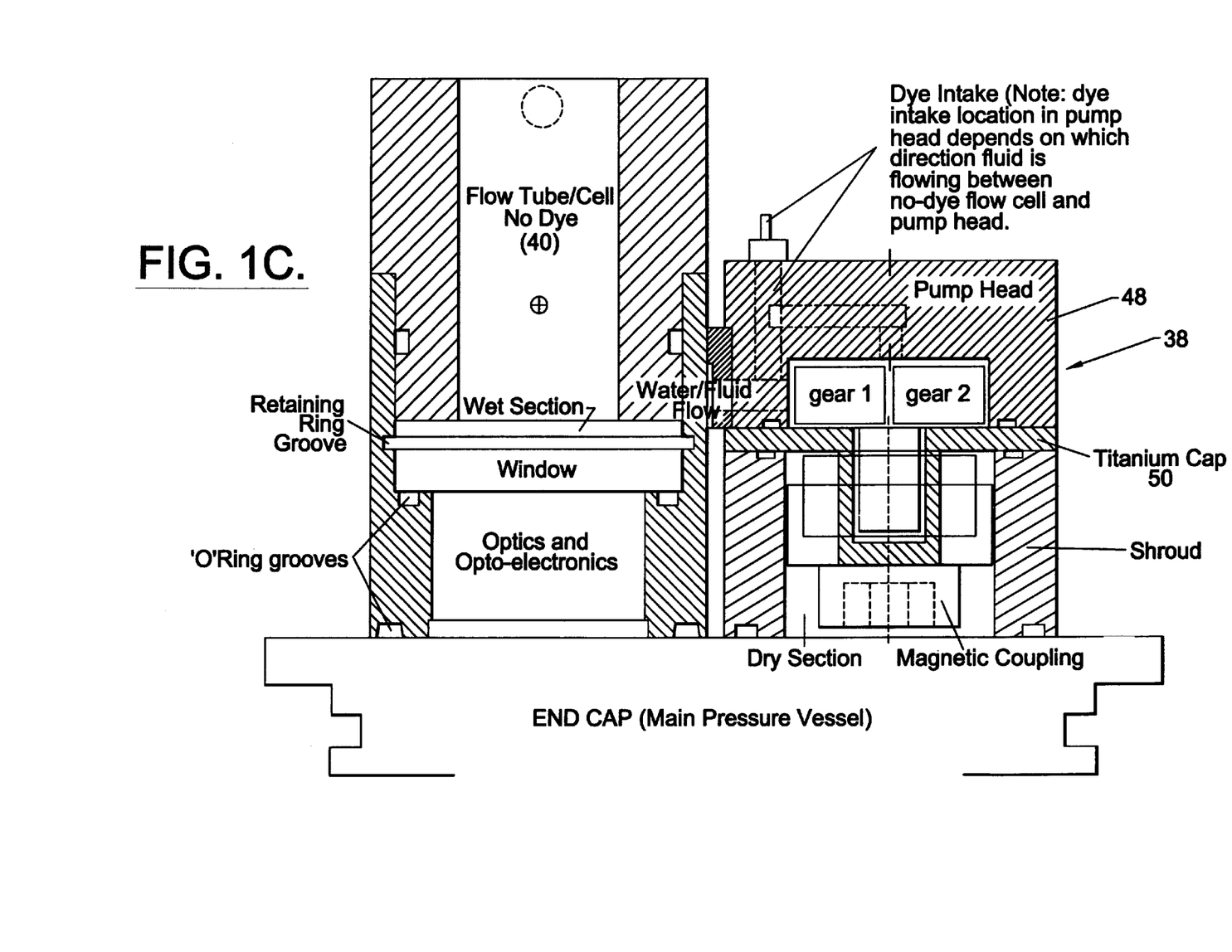
FIG. 1C is a fragmentary sectional view of the vessel of FIGS. 1, 1A and 1B, taken from the direction 1C—1C in FIG. 1B, with portions omitted.

The design goals for the in situ pH sensor are given in Table 1. As can be seen from Eq. (1), seawater temperature, salinity, and thymol blue absorbance at two wavelengths are required for the pH determination, and depth is required for sample location. The vessel $10$ for the pH sensor is shown in FIGS. 1A–1C and a functional block diagram of the vessel is shown in FIG. 2. A Falmouth Scientific Conductivity Temperature Depth Probe (CTD), comprising probes $32$, $34$ and electronic component $22$, was used to provide the salinity, temperature, and depth data.

TABLE 1

| In Situ Sensor Design Goals |
| --- |
| pH resolution: ±0.001 |
| Operating Depth: 500 m |
| Measurement frequency: 1 Hz |
| Standalone or real-time operation |
| Data storage within sensor |
| Deployment time: 1 hour |
| Continuously meter in indicator at constant mix ratio |
| Primary indicator is thymol blue - maintain compatibility with other indicators such as m-cresol purple |

2.1.1 Optical Design

Several different optical sources, elements, and detectors were experimentally evaluated. Within size and cost limitations, a design employing interference filters for wavelength selection was given preference over a grating spectrometer. Within each flow cell $40$, $42$, absorbance measurements at three wavelengths are performed. Two of these wavelengths are directly used for computation (Eq. 1), and the third wavelength, in the near-infrared, is used for monitoring high-frequency absorbance variations that are not related to thymol blue.

Light-emitting diodes (LEDs) $28$ were selected as optical sources for the following reasons: (1) they are commercially available with emitting wavelengths ranging from the low 400 nm range up into the near-infrared (considering their wide spectral widths); (2) they are inherently more reliable than incandescent and halogen-type lamps; and (3) they are small and inexpensive. In order to improve the collimation of the LED, a 4-mm-diameter gradient index (GRIN) lens (NSG America) was butt-coupled to the LED after the plastic lens of the LED was polished away. Given the limited variety of LEDs for use in the blue region, a Nichia "1000 mcd" LED was selected for our application (peak wavelength 450 nm, ≠70 nm spectral half-width). A Toshiba "8000 mcd" LED (peak wavelength 590 nm, ·90 nm FWHM spectral width) was used for the 596 nm absorbance measurement.

For our application ($0.2 \leq {}^\lambda A \leq 0.8$) we were interested in concentrating as much light as possible onto the detector's active area (2.3 mm square), about 12 cm from the source. By shortening a 0.25-pitch GRIN lens, it was possible greatly to improve the intensity of light on the detector's active area. An integrated photodiode and amplifier (Burr-Brown OPT201) was chosen for its gain, noise, and size characteristics.

The absorbance terms ($^{596}A$ and $^{435}A$) in Eq. (1) refer to the incremental absorbances due to the addition of thymol blue to seawater. In terms of optical power measurements, the absorbance ratio term can be written as:

$$R = {}^{596}A/{}^{435}A = \log({}^{596}P_{wi}/{}^{596}P_{wo})/\log({}^{435}P_{wi}/{}^{435}P_{wo}) \quad (2)$$

where $^\lambda P_{wi}$ is the optical power measured with added indicator at wavelength $\lambda$ and $^\lambda P_{wo}$ is the optical power measured without indicator (seawater only).

Further details of the optical sensor circuitry are shown in FIGS. 3, 4 and 5A–5D. Also, while the embodiment disclosed herein shown the LED's 28 and the detectors 30 on opposite sides of the optical flow cells, it is possible to provide both the LED's and the detectors disposed on the same side of the optical flow cells, with each flow cell having a concave spherical mirror (e.g., with a 50 mm focal length) provided in the optical flow to fold the light back onto the associated detector. In such an embodiment, there would be only one, rather than two sealed compartments making up the sealed portion of the vessel.

2.1.2 Fluid/Mechanical Design

To achieve the goal of one reading per second, a "continuous flow" sensor was employed. This choice resulted in some potentially problematic design features (i.e., separate measurement cells), which we have addressed. The first (or "no dye") flow cell 40 performs optical measurements on seawater alone, and the second (or "dye") flow cell 42 performs measurements on the seawater/indicator mixture. Intercell calibration of the optical measurements between the two flow cells is addressed in a later section.

After reviewing the variety of pumps that could be adapted for underwater applications, an Instech peristaltic pump 44 was selected for delivery of indicator solution with a flow rate of 200 λliter/minute. The seawater's flow rate was initially set to 0.4 liter/minute. FIG. 1C shows further schematics of the gear pump 38 assembly. A DC motor 26 mounted to the inside of the main pressure chamber 12A drives a magnetically coupled gear pump 38 assembly through a titanium cap 48 that is O-ring sealed. A pump head 50, fitted over the gear pump 38, couples fluid to and from the flow cells. "In-line" mixers are utilized to mix the indicator and water.

The sensor was originally designed for deployment in a vertical orientation (i.e., with the vessel 10 in the orientation shown in FIG. 2). In this orientation, attempts to have the sensor automatically expel bubbles were met with limited success. A successful approach to this important problem was devised by deploying the sensor in an orientation close to horizontal to allow air to escape from the pump head and flow cells, having electronic control of the main pump, and performing a predetermined start and stop sequence, at normal and faster than normal flow rates, in a manner described below in Section 2.2.1.

The pressure-bearing sealed portion 12 was designed to withstand depths of 500 m. Pressure tests demonstrated that the sensor was capable of operation at depths of 650 m without catastrophic failure.

2.1.3 Electronic Design

A commercially available microcontroller 18 (Blue Earth) was utilized for control within the sensor, including communications to a remote computer. Circuitry and software were designed such that the sensor would perform startup operations and calibrations upon entering the water. The startup established the sensor's overall operating mode (i.e., standalone, real-time, or data download), initiated a bubble elimination sequence, and provided for CTD initialization. The sensor's electronics utilized a 12-bit A/D converter to digitize six signals, three from each flow cell. The seawater/indicator mix ratio was adjusted from 1000:1 to 2200:1 so that the voltage levels were near the middle of the A/D converter's range. This promotes the goal of minimizing indicator consumption.

The sensor requires +12 V at 1 A maximum operating conditions. The sensor utilizes RS-422 communication protocol, which, in this implementation, is RS-232 compatible. The sensor is also designed to communicate over Echelon's LonWorks Network.

Further details of the electronic circuitry of this embodiment are shown in FIGS. 3, 4, 5A–5D and 6.

2.2 pH Sensor Embedded Software

The embedded software for the pH sensor comprises several different files loaded onto a Blue Earth microcontroller, an 8051-based control module. The files are written in either Blue Earth Basic or Assembly Language and are stored in battery-backed RAM on the Blue Earth.

The controller (i.e., main board 16 and microcontroller 18) is interfaced to a CTD instrument 22 built into the sensor, which it polls once per second for updates. This is a serial (9600 baud) interface. The controller also has four analog-to-digital converters (ADCs) on board, which are utilized for data collection. The controller has several control lines, which are used to control the sensor main pump, dye pump, and LEDs. The controller is also interfaced to a LonWorks control module 20 (see also FIG. 6) to allow data collection in this format.

The controller is set up to autoexecute upon power up into one of four modes of operation. The mode is determined by reading cable jumpers. The four modes are:

Normal operation—Data are stored as they are collected in a standalone operating mode.

Real-time operation—Data are reported as they are collected (serially at 19200 baud) to a host computer. Local storage is also possible. An operator can intervene into the controller's normal operation by pressing one of several designated keys on the host computer's keyboard.

Data offload—Stored data are offloaded to a host computer serially at 19200 baud. This is an ASCII download of the ADC and CTD data logged in a previous run. The operator will have an opportunity to reset the data logging pointers at the end of the data offload.

LON controlled—Data are communicated over the network as they are collected. The normal operation can be altered by changing the appropriate network variables.

The controller has nearly 64K of memory available for storage. The CTD 22 also has 1 Meg of memory, which is used to log its readings.

2.2.1 Typical Operation

The sensor begins collecting data immediately upon power up, but little of consequence occurs until it realizes that it has entered the water. This determination is made from the periodic CTD readings.

A sequence to eliminate bubbles from the sensor mixing chamber is initiated when the sensor is in the water. The controller waits for 20 seconds, and then initiates the main pump at a high speed for 20 seconds. The pump is then shut down for 5 seconds, followed by a normal-speed turnon. Data logging is enabled at this point. The CTD 22 is opened up for data logging, and the Blue Earth controller begins to log the ADC readings. Each ADC is read 8 times, and the average reading is logged.

A self-calibration routine is then initiated. Approximately ninety seconds of no-dye baseline readings are performed, the first 5 seconds of which are dark readings made with all LEDs turned off. The dye pump is turned off for the duration of this baseline calibration routine. The dye pump is turned on when a depth of 50 meters is reached (as read from the CTD). This self-calibration routine is done every 15 minutes as long as the sensor remains powered up in the water.

The controller continues to log data until its 64K of memory is fill, or until it is brought out of the water. The data are stored in battery-backed RAM; power may be turned off to the sensor without losing any data. In the real-time mode, the controller will continue to collect data and send it to the host computer after its local memory is full.

Debugging messages can be printed to the host computer by altering the contents of one byte within the controller. A utility program is also included in the controller to allow direct communication from a host computer to the CTD 22, enabling CTD parameters to be altered directly.

2.2.2 pH Sensor PC-Based Software Description

User functions:

Start data acquisition

Stop data acquisition

Offload/dump data

Real-time data mode

Graph existing data file

Development menu

Command mode

Retrieve data

Header information

Data/time—user input, PC date/time as default

File name

Cast number—3 digits

Latitude/longitude

User name

Cruise name

Calibration constants

Sensor—pH sensor 1 or 2

Data filter increment—i.e., retain every 60th (minute's) reading

Absorbance of dye—R

Comment field

Real-time mode

Plot pH, salinity, temperature vs. depth/pressure—3 (pH, salinity, T) separate areas along x axis representing depth. Depth expressed in decibars (see, e.g., FIG. 7). Plot will initially move down from upper left corners of area. Upper lefts represent sea level. Since depth is time-variant, the graph grows down as time and depth increase (see, e.g., FIG. 7).

User functions and appropriate menus shall be accessible via function keys.

Offload mode

When appropriate, the PC shall accept the serial stream of raw data from the sensor (format defined elsewhere). The baud rate is 19,200, no parity, 1 start/stop bit. The data shall be stored in a raw data file. The name of that file shall be selectable by the user. The header information (defined elsewhere) shall also be entered by the user at this time. User-defined parameters shall then be sued to filter the raw data and store it in another file.

Command mode

When connected to a PC running a terminal emulation program, various commands can be sent to the pH sensor for test and evaluation. Those commands are:

| P | main pump on | p | main pump off |
|---|---|---|---|
| D | dye pump on | d | dye pump off |
| L | LEDs on | l | LEDs off |
| M | memory log on | m | memory log off |
| F | fast forward mode on | f | fast forward mode off |
| R | reset data pointer | | |
| ctrl-x | shutdown sensor | | |
| g | start sensor | | |

Serial records from the sensor

Sent during real-time mode or during offload/data dump as comma-delimited record terminated by a carriage return. During offload/data dump operations, the Blue Earth data (see first table) for the entire run shall be sent up first. The CTD for the entire run shall then follow (see Table 3). The Blue Earth data shall then be synchronized with the CTD data in sequence—first Blue Earth record with first CTD record. The assumption is that both these sets of data were synchronized by Blue Earth during the data gathering process. During real-time operations, both sets of data will have to be sent up together every second. Similar to the offload mode, CTD data will follow the Blue Earth data but in one record. The format for the data is as in Table 2.

TABLE 2

| Status | | 1 byte meaning bits TBD |
|---|---|---|
| Dye A (blue dye) | $P_{db}$ | 2 bytes integer |
| Dye B (orange dye) | $P_{do}$ | 2 bytes integer |
| No Dye A (no blue dye) | $P_{nb}$ | 2 bytes integer |
| No Dye B (no orange dye) | $P_{no}$ | 2 bytes integer |
| Dye IR (IR dye) | $P_{ir}$ | 2 bytes integer |
| No Dye IR (no IR dye) | $P_{nir}$ | 2 bytes integer |

TABLE 3

| Conductivity (mho/cm) | floating point in ASCII string XXX.XXX |
|---|---|
| Temperature (° C.) | floating point in ASCII string XX.XX |
| Pressure (decibar) | floating point in ASCII string XXX.XX |
| Time | TBD |

Status—e.g., pump on/off and dark measurement.

Data storage

All raw data are saved in comma-delimited, carriage-return-terminated record file using the following format: Status, A/D1, A/D2, A/D3, A/D4, A/D5, A/D6, conductivity, temperature, depth, absorption 1, absorption 2, pH (PC-based calculation).

User's filtered data

ASCII fields, comma-delimited, carriage-return-terminated using the following format (suitable for Excel): raw data record #, pH, salinity, depth, temperature, absorption 1, absorption 2.

User will have the option of filtering the data via time. For example, raw records, obtained every second, could be filtered to retain only 1 of 60 seconds worth of values. This is a user-selectable parameter. A field indicating the record's original position in the raw file shall be retained in the new filtered record.

This filtering feature shall be available for both immediately offloading data as well as later processing of archived raw data files.

Additional features of the foregoing PC-based software

Flexibility of on-board data storage or real-time serial link to a deckside PC. On-board data storage enables the sensor to be deployed on casts without a communications link. Acquired data can then be offloaded to a PC after the cast. Alternately, if serial communications are available, data can be received and viewed deckside as they are acquired.

Outputs of deckside PC include both graphical displays of pH, salinity, and temperature versus depth and comma-delimited data files for future analysis.

The test mode of the pH sensor allows various subsections of the instrument to be exercised without going through the full data acquisition/calculation cycles. Tasks enabled by the test mode include control of the separate motors as well as sensor memory manipulation.

2.3 Instrument Evaluation

The instrument is programmed to take absorbance readings once per second. Absorbance acquisition at 1 Hz results in pH oversampling for the following reasons: The volume of the flow cells and the flow rate is such that the volume is completely exchanged every 12 seconds. Second, the indicator's flow rate is not constant, owing to 0.25 Hz pulsations at the peristaltic pump head. Thus a moving average with a period of 12 seconds, a multiple of both periods, was employed for pH calculations.

2.3.1 Intercell Calibration

Instead of calibrating each measurement cell independently, cells were calibrated in a relative sense. Accordingly Eq. (2) becomes:

$$R = \log[C_o(^{596}P_{wi}/^{596}P_{wo})]/\log[C_b(^{435}P_{wi}/^{435}P_{wo})] \quad (3)$$

with $C_o = (^{596}P_{wo}/^{596}P_{wi})_{\text{without indicator in system}}$ and $C_b = (^{435}P_{wo}/^{435}P_{wi})_{\text{without indicator in system}}$ It was initially thought that this intercell calibration would be required relatively infrequently. However, two variables (size and location of bubbles and salt residue on mirrors and windows) dictated an intercell calibration on each cast. Intercell calibration is performed automatically at the start of a cast by calculating $C_o$ and $C_b$ factors prior to pumping indicator into the flow cell. This automatic intercell calibration eliminates some of the maintenance an operator would otherwise perform between casts. In other words, windows and mirrors do not need to be spotless prior to each deployment. Flushing the cells with tap water after each cast is adequate maintenance for this system.

2.3.2 Temperature Compensation

Several of the components in the optical measurements require temperature compensation. This compensation is performed by measuring the temperature dependence of each channel and applying compensation factors. With temperature compensation factors, Eq. (3) becomes:

$$R = \frac{\log\{C_o[^{596}P_{wi}(1-\Delta t \cdot S_{oi})]/^{596}P_{wo}(1-S_{oo})]\}}{\log\{C_b[^{435}P_{wi}(1-\Delta t \cdot S_{bi})]/^{435}P_{wo}(1-S_{bo})]\}} \quad (4)$$

where $\Delta t$ is the difference between the temperature at which $C_o$ and $C_b$ were determined and the current pH measurement temperature, and $S_{bi}$, $S_{oi}$, $S_{bo}$, and $S_{oo}$ are laboratory-determined compensation factors.

2.4 Standard Deployment

Given the intended mission scenarios and the previously described calibration requirements, standard deployment proceeds as follows. Once power is applied to the sensor, the sensor remains in standby mode until it enters the water. At this point in time, intercell calibration and preprogrammed bubble elimination processes are initiated. Since these are critically important processes, the software prescribes a minimum time and depth before the standard measurement mode is initiated. As such, surface water pH is measured only on the up cast. This sacrifice generally results in loss of initial data to a depth of 50 m provided the down cast is not extremely rapid. The sensor acquires pH data until it exits the water. For initial deployments the sensor was programmed to repeat the intercell calibration every 15 minutes.

The above scenario describes a data logging deployment, in which case sensor data are not monitored in real time and the sensor mission is preprogrammed. With a sensor operating in real-time mode, the sensor can be held just under the surface until the acquisition mode is initiated. In this preferred operating mode, the user is in complete control of all sensor functions with optional bypass of predefined setpoints.

2.5 Test Results

Several types of experiments were attempted to quantify sensor precision. Unfortunately, we were not able to develop a fully satisfactory laboratory evaluation. In the laboratory it is difficult to ensure that a large tank of water has constant pH over a long experiment in which the sensor is discharging thymol blue into the test tank. Other effects such as $CO_2$ exchange between the atmosphere and water also may affect pH in the thousandths and ten-thousandths of a pH unit range.

2.6 Cruise Results

Figure 7:
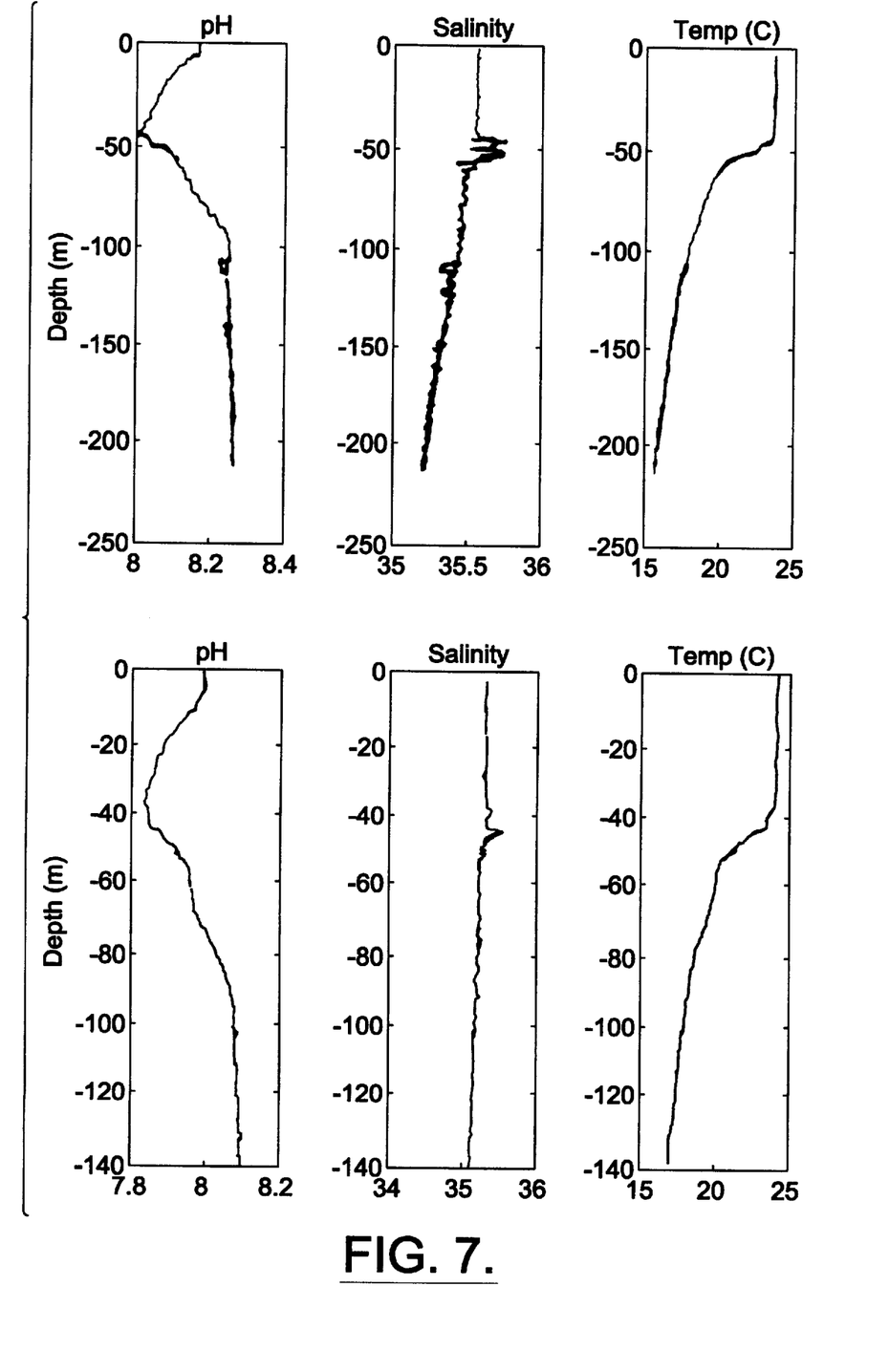
FIG. 7 illustrates typical pH, salinity and depth profiled from the South Pacific and Antarctic Oceans, using an early version of a pH sensor according to the principles of the present invention.

An earlier version of the sensor was deployed in the South Pacific and Antarctic Oceans during NOAA $CO_2$-system investigations (January–March 1996) aboard the R/V Discoverer. The sensor was deployed once a day for a total of roughly 60 casts. FIG. 7 shows the pH, salinity, and temperature recorded on two casts. Most of the casts' pH distributions had similar shapes. This figure exhibits some of the oceanic $CO_2$-system microstructure that can be revealed with precise in situ pH instrumentation.

3. PARTS PROVIDERS

Parts providers referenced in this application are described in Attachment A.

4. CONCLUSION

The foregoing description illustrates an in situ pH sensor for use with seawater. With the foregoing description in mind, the manner in which the principles of the present invention can be used to create an in situ sensor for other aqueous medium will be apparent to those skilled in the art.

What is claimed is:

1. A device for in situ pH measurement of an aqueous medium comprising means for determining salinity and temperature of the aqueous medium, means for adding indicator to the aqueous medium to form a mixture, and means for spectrophotometrically analyzing the absorbance characteristics of the aqueous medium/indicator mixture to enable determination of the pH of the aqueous medium.

2. Apparatus for use in conducting in Situ pH analysis of an aqueous medium, comprising a vessel for immersion in the aqueous medium, said vessel comprising:

a sealed portion and a wet portion, said sealed portion containing electronic and opto-electronic components and being substantially sealed from contact with the aqueous medium, said wet portion comprising (i) one or more probes in direct contact with the aqueous medium, and (ii) an optical flow channel through which a portion of the aqueous medium in which the vessel is immersed is directed at a substantially continuous controlled rate, said vessel further including means for introducing indicator into the portion of the aqueous medium flowing through the optical flow channel at a selected location in the optical flow channel to form an aqueous medium/indicator mixture; said opto-electronic components being disposed in a predetermined orientation to said optical flow channel to provide optical power inputs related to the absorbance characteristics of the portion of the aqueous medium/indicator mixture flowing through the optical flow channel; said electronic components being adapted to receive and process inputs from said probes and said opto-electronic components at a frequency which enables substantially continuous determination of the pH of the aqueous medium in which the vessel is immersed.

3. The apparatus as set forth in claim 2, further including data transmission means for transmitting data from said sealed portion of said vessel to a receiving station outside of the aqueous medium.

4. A method for providing in Situ measurements of an aqueous medium, comprising the steps of:

immersing in the aqueous medium a vessel for comprising a sealed portion and a wet portion, the sealed portion containing electronic and opto-electronic components and being substantially sealed from contact with the aqueous medium, the wet portion comprising (i) one or more probes in direct contact with the aqueous medium for providing input related to the temperature and salinity of the aqueous medium; and (ii) an optical flow channel through which a portion of the aqueous medium in which the vessel is immersed can be directed at a substantially continuous controlled rate, and into which an indicator can be introduced at a selected location to form an aqueous medium/indicator mixture, the opto-electronic components being disposed in a predetermined orientation to the optical flow channel to provide optical power inputs related to the absorbance characteristics of the portion of the aqueous medium/indicator mixture flowing through the optical flow channel in a state of chemical equilibrium; the electronic components being adapted to receive and process inputs from the probes and opto-electronic components at a frequency which enables substantially continuous determination of the pH of the aqueous medium in which the vessel is immersed;

initiating a substantially continuous flow of the aqueous medium through the optical flow channel, and introducing indicator into the aqueous medium at the selected location in the optical flow channel to form an aqueous medium/indicator mixture in the optical flow channel; and providing and processing inputs from the probes and the opto-electronic components at a frequency rate that approximates substantially continuous sampling of the aqueous medium and enables substantially continuous determination of the pH of the aqueous medium.

5. A method as set forth in claim 4, further including the step of transmitting data related to the pH measurements to a station remote from the aqueous medium.

6. A method as set forth in claim 5, wherein the aqueous medium is seawater.

7. A method as set forth in claim 4, wherein the aqueous medium is seawater.

* * * * *